United States Patent [19]

Minor et al.

[11] Patent Number: 4,857,634
[45] Date of Patent: Aug. 15, 1989

[54] PEPTIDES USEFUL IN VACCINATION AGAINST ENTEROVIRUSES

[75] Inventors: Philip D. Minor, London; David M. A. Evans, Hertfordshire; Geoffrey C. Schild, London; Jeffrey W. Almond, Leicester; Morag Ferguson, Hertfordshire, all of England

[73] Assignee: National Research Development Corporation, London, England

[21] Appl. No.: 89,037

[22] Filed: Aug. 24, 1987

Related U.S. Application Data

[63] Continuation of Ser. No. 847,455, Apr. 3, 1986, abandoned.

[30] Foreign Application Priority Data

Apr. 3, 1985 [GB] United Kingdom ................. 8508685

[51] Int. Cl.$^4$ .......................... C07K 7/06; C07K 7/08; C07K 7/10; A61K 39/12
[52] U.S. Cl. .................................... 530/324; 530/325; 530/326; 530/327; 530/328; 530/329; 530/330; 530/331; 530/403; 435/7; 424/88; 424/89
[58] Field of Search ............... 530/324, 325, 326, 327, 530/328, 329, 330, 331, 403; 514/18, 17, 16, 15, 14, 13, 12; 435/7; 424/89, 88

[56] References Cited

U.S. PATENT DOCUMENTS 4,544,500 10/1985 Bittle et al. .................. 260/112.5 R
4,554,101 11/1985 Hopp ............................ 260/112.5 R
4,694,071 9/1987 Almond et al. ..................... 530/329

FOREIGN PATENT DOCUMENTS 0044710 1/1982 European Pat. Off. .
0065924 12/1982 European Pat. Off. .
0068719 1/1983 European Pat. Off. .
0076489 4/1983 European Pat. Off. .
0086707 8/1983 European Pat. Off. .
0107436 5/1984 European Pat. Off. .
0110791 6/1984 European Pat. Off. .
WO82/03632 10/1982 PCT Int'l Appl. .
WO82/04067 11/1982 PCT Int'l Appl. .
WO83/03547 10/1983 PCT Int'l Appl. .
WO83/03972 11/1983 PCT Int'l Appl. .
2108510 5/1983 United Kingdom .
2128621 5/1984 United Kingdom .

OTHER PUBLICATIONS

Kitamura et al, Nature, vol. 291, pp. 547–553 (1981).
Evans et al, Nature, vol. 304, pp. 459–462 (1983).
Fricks et al, Journal of Virology, vol. 54, No. 3, pp. 856–859 (1985).
Minor et al, Chem. Abstr., vol. 105, No. 75533w (1986).
Minor et al., Applied Virology, pp. 31–49 (1984).
Minor et al., Review of Infectious Diseases, vol. 6, Supp. 2, pp. S516–S518 (1984).
Stanway et al., European Journal of Biochemistry, vol. 135, pp. 529–533 (1983).
Stanway et al., J. Virol., pp. 1187–1190 (3/1986).
J. Mol. Biol (1984), 174, pp. 561–585, "Complete Nucleotide Sequences of All Three Poliovirus Serotype Genomes", *Toyoda et al.*
"Poliomyelitis–Epidemiology, Molecular Biology and Immunology", P. D. Minor et al, Nature, vol. 299, Sep. 9, 1982, pp. 109–110.
"Primary Structure, Gene Organization and Polypeptide Expression of Poliovirus RNA", Kitamura et al, Mature, vol. 291, Jun. 18, 1981, pp. 547–553.
"Complete Nucleotide Sequence of the Attenuated Poliovirus Sabin 1 Strain Genome", A. Nomoto et al, Proc. Natl. Acad. Sci. USA, vol. 79, Oct. 1982, pp. 5793–5797.

(List continued on next page.)

*Primary Examiner*—Delbert R. Phillips
*Assistant Examiner*—Christina Chan
*Attorney, Agent, or Firm*—Oblon, Fisher, Spivak, McClelland & Maier

[57] ABSTRACT

A synthetic peptide, suitable for use in vaccination against or diagnosis of a disease caused by an enterovirus and especially by a poliovirus, is the peptide coded for by codons 286-290 in the RNA sequence coding for the structural capsid protein VP1 of poliovirus type 3 Sabin strain or by equivalent codons of another enterovirus or is an antigenic equivalent thereof, the numbers of the codons being counted from the 5'-terminus of the nucleotide sequence coding for the VP1 capsid protein.

21 Claims, 1 Drawing Sheet

| | | | | | | | | | | | |
|---|---|---|---|---|---|---|---|---|---|---|---|
| GGU* | AUU | GAA | GAU | UUG | AUU | UCU | GAA | GUU | GCA | CAG | GGC |
| GCC | CUA | ACU | UUG | UCA | CUC | CCG | AAG | CAA | CAG | GAU | AGC |
| UUA | CCU | GAU | ACU | AAG | GCC | AGU | GGC | CCG | GCG | CAU | UCC |
| AAG | GAG | GUA | CCU | GCA | CUC | ACU | GCA | GUC | GAG | ACU | GGA |
| GCC | ACC | AAU | CCU | CUG | GCA | CCA | UCC | GAC | ACA | GUU | CAA |
| ACG | CGC | CAC | GUA | GUC | CAA | CGA | CGC | AGC | AGG | UCA | GAG |
| UCC | ACA | AUA | GAA | UCA | UUC | UUC | GCA | CGC | GGG | GCG | UGC |
| GUC | GCU | AUU | AUU | GAG | GUG | GAC | AAU | GAA | CAA | CCA | ACC |
| ACC | CGG | GCA | CAG | AAA | CUA | UUU | GCC | AUG | UGG | CGC | AUU |
| ACA | UAC | AAA | GAU | ACA | GUG | CAG | UUG | CGC | CGU | AAG | UUG |
| GAG | UUU | UUC | ACA | UAC | UCU | CGU | UUU | GAC | AUG | GAA | UUC |
| ACC | UUC | GUG | GUA | ACC | GCC | AAC | UUC | ACC | AAC | GCU | AAU |
| AAU | GGG | CAU | GCA | CUC | AAC | CAG | GUG | UAC | CAG | AUA | AUG |
| UAC | AUC | CCC | CCA | GGG | GCA | CCC | ACA | CCA | AAG | UCA | UGG |
| GAC | GAC | UAC | ACU | UGG | CAA | ACA | UCU | UCC | AAC | CCG | UCC |
| AUA | UUU | UAC | ACC | UAU | GGG | GCU | GCC | CCG | GCG | CGA | AUC |
| UCA | GUG | CCA | UAC | GUG | GGG | UUA | GCC | AAU | GCU | UAC | UCG |
| CAC | UUU | UAC | GAC | GGC | UUC | GCC | AAG | GUG | CCA | UUG | AAG |
| ACA | GAU | GCC | AAU | GAC | CAG | AUU | GGU | GAU | UCC | UUG | UAC |
| AGC | GCC | AUG | ACA | GUU | GAU | GAC | UUU | GGU | GUA | UUG | GCA |
| GUU | CGU | GUU | GUC | AAU | GAU | CAC | AAC | CCC | ACU | AAA | GUA |
| ACC | UCC | AAA | GUC | CGC | AUU | UAC | AUG | AAA | CCC | AAA | CAC |
| GUA | CGU | GUC | UGG | UGC | CCU | AGA | CCG | CCG | CGC | GCG | GUA |
| CCU | UAU | UAU | GGA | CCA | GGG | GUG | GAC | UAU | AGG | AAC | AAC |
| UUG | GAC | CCC | UUA | UCU | GAG | AAA | GGU | UUG | ACC | ACA | UAU |

* no 1

PEPTIDES USEFUL IN VACCINATION AGAINST ENTEROVIRUSES

This application is a continuation of application Ser. No. 847,455 filed on Apr. 3, 1986, now abandoned.

This invention relates to peptides having biological activity, particularly for use in vaccines for diseases caused by enteroviruses and in particular polioviruses.

Polioviruses are divisible into three serotypes on the basis of their neutralization reactions with specific immune sera. However, they have similar virological properties and clinical effects and the nucleic acid and amino-acid sequences of all three serotypes are strikingly similar (Stanway et al Nucleic Acids Research 11, 5629–5643, 1983; Stanway et al Proc. Natl. Acad. Sci. U.S.A. 81, 1539–1543, 1984).

We have previously identified the location of a single major antigenic site involved in the neutralization of poliovirus type 3 (Minor et al, Nature 301, 674–679, 1983; Evans et al, Nature 304, 459–462, 1983). In GB-A-2 128 621 we have described and claimed a synthetic polypeptide, suitable for use in vaccination against or diagnosis of a disease caused by an enterovirus, which comprises an antigenically effective hexapeptide coded for by codons 93 to 98 in the RNA sequence coding for the structural capsid protein VP1 of a poliovirus type 3 Sabin strain or by equivalent codons of another enterovirus. The codon numbers herein are counted from the 5'-terminus of the nucleotide sequence coding for the VP1 capsid protein.

In contrast to this, it has been suggested that neutralization of poliovirus type 1 involves multiple independent antigenic sites (Emini et al J. Virol. 46, 466–474, 1983). If correct, this difference between closely related viruses would make the satisfactory prediction of viral peptide sequences for use as vaccines more difficult than hitherto supposed.

We have now identified a second antigenically significant peptide coded for by an RNA sequence within the genome region coding for the structural capsid protein VP1 of an enterovirus.

Accordingly, the present invention provides a synthetic peptide, suitable for use in vaccination against or diagnosis of a disease caused by an enterovirus, which is coded for by codons 286 to 288, preferably by codons 286 to 290, in the RNA sequence coding for the structural capsid protein VP1 of a poliovirus type 3 Sabin strain or by equivalent codons of another enterovirus or is an antigenic equivalent thereof.

The peptides of the invention therefore comprise an antigenically effective peptide unit coded for as indicated. They are not naturally-occurring peptides, such as the VP1 capsid protein itself, which have been recovered in a suitably pure form after disrupting an enterovirus. Rather, the hand of man has been involved in the making of the peptides of the invention. In particular, the peptides of the invention can be prepared by chemical synthesis from single amino acids or smaller preformed peptides; or by employing the methods of genetic engineering to produce an organism which makes the peptides in recoverable form.

By "equivalent codons" is meant a sequence of codons in the RNA sequence coding for the structural capsid protein VP1 of another enterovirus, corresponding to the codon sequence 286–288 or 286–290 in the RNA sequence coding for the structural capsid protein VP1 of the poliovirus type 3 Sabin strain. The "equivalent codons" are therefore the counterpart codons in the RNA sequence coding for the capsid protein VP1 of another enterovirus to codons 286–288 or 286–290 for the poliovirus type 3 Sabin strain.

The counterpart codons can readily be determined by lining up the base sequence coding for the VP1 protein in the RNA sequence of another enterovirus with the corresponding base sequence of the poliovirus type 3 Sabin strain. While it is possible that the equivalent codons in the other enterovirus may also be 286–288 or 286–290, this is not necessarily the case. In the poliovirus type 3 Leon strain, which is the virulent progenitor of the attenuated Sabin strain, the equivalent codons are 286–288 or 286–290. The equivalent codons are 286–288 or 286–290 too for the poliovirus type 2 Sabin strain. However, in the poliovirus type 1 Sabin strain, there are four equivalent codons, 287–290, or six equivalent codons, 287–292, as the case may be. Thus, when the base sequences for the Sabin strains of each of the three types of poliovirus are lined up (Toyoda et al, J. Mol. Biol. 174, 561–585, 1984), the result is as follows:

| type 3 | Sabin:codon | 286 | 287 |     | 288 | 289 | 290 |
|--------|-------------|-----|-----|-----|-----|-----|-----|
|        |             | AGG | AAC |     | AAC | UUG | GAC |
| type 2 | Sabin:codon | 286 | 287 | 288 |     | 289 | 290 |
|        |             | AAA | GAU | GGG |     | CUC | ACC |
| type 1 | Sabin:codon | 287 | 288 | 289 | 290 | 291 | 292 |
|        |             | AAG | GAU | GGU | ACG | CUU | ACA |

An "antigenic equivalent" of any particular "natural" peptide sequence coded for by an existing enterovirus (whether wild-type or mutant) is a peptide which, if not itself immunogenic, when linked to material which renders it immunogenic is capable of inducing the same or a very similar antibody response as the "natural" peptide, i.e. the antibody produced, though possibly not precisely identical, would neutralize the same strain and type of enterovirus and hence antigenicity is effectively equivalent.

An antigenic equivalent of a "natural" peptide sequence may be a peptide of the same length which, however is not coded for by a wild-type or known mutant enterovirus but includes one or more changes to the amino acids in the sequence which does not affect the antigenicity. Thus, one or more amino acids of a "natural" peptide sequence may be replaced by, respectively, one or more other amino acids which preserve the physico-chemical character of the original, i.e. in terms of charge density, hydrophilicity/hydrophobicity, size and configuration, and hence preserve the immunological structure. For example, Thr may be replaced by Ser and vice versa, Asp may be replaced by Glu and vice versa and Asn may be replaced by Gln and vice versa.

An antigenic equivalent may also be a longer peptide which comprises a "natural" peptide sequence but still has equivalent antigenicity. The "natural" peptide sequence will thus be exposed in the longer peptide so as to be available to induce the appropriate immune response and not "buried" in the interior of the longer peptide and consequently unable, itself, to provoke an immune response.

Yet further antigenic equivalents may be formed by modifying reactive groups within a "natural" sequence or modifying the N-terminal amino and/or C-terminal carboxyl group. Such equivalents can include salts formed with acids and/or bases, particular physiologically acceptable inorganic and organic acids and bases. Other equivalents may include modified carboxyl groups to produce esters or amides or may include typical amino acid protecting groups such as N-t-butoxycarbonyl. Preferred modifications of this type are those which enable the production of a more stable, active peptide which will be less prone to enzymic degradation in vivo.

A combination of two or more of the types of variations of a "natural" sequence described above may be used to arrive at an antigenic equivalent peptide of the invention. For example, a peptide sequence which has been derived from a "natural" sequence by changing one or more of the amino acids in the "natural" sequence may be incorporated in a longer peptide.

The present invention will now be described with particular reference to polioviruses, though it will be appreciated that the concept of the invention is considered to apply equally well to other enteroviruses, i.e. viruses which are found in the intestine, e.g. ECHO (Enteric Cytopathic Human Orphan) and Coxsackie B viruses. In accordance with convention, the bases referred to herein are as follows:

A = Adenine
G = Guanine
C = Cytosine
U = Uracil.

Similarly, in accordance with convention, the following abbreviations are used for the amino acid radicals:

Alanine = Ala
Arginine = Arg
Asparagine = Asn
Aspartic acid = Asp
Cysteine = Cys
Glutamine = Gln
Glutamic Acid = Glu
Glycine = Gly
Histidine = His
Isoleucine = Ile
Leucine = Leu
Lysine = Lys
Methionine = Met
Phenylalanine = Phe
Proline = Pro
Serine = Ser
Threonine = Thr
Tryptophan = Trp
Tyrosine = Tyr
Valine = Val Wherever these amino acids are mentioned, they cover both the D- and L-configurations. However, it is preferred in accordance with the invention that the amino acids should take the natural, i.e. the L-, configuration.

The Figure of the accompanying drawing shows the RNA sequence for the VP1 capsid protein in the poliovirus type 3 Sabin strain. Within this sequence, codons 93-98 and 286-290 are underlined.

It has not yet been unequivocally established whether the nucleotide sequence coding for the VP1 capsid protein of the poliovirus type 3 Sabin strain actually commences with the codons GGU AUU ... as shown in the Figure or with the codon GGC ... which is the twelfth codon in the Figure. Nevertheless, herein the codons for the nucleotide sequence of the VP1 capsid protein of poliovirus type 3 Sabin strain are counted from the first codon in the Figure, GGU.

In accordance with this notation, the appropriate RNA sequence coded for by codons 286-288 for Sabin type 3 poliovirus and the corresponding tripeptide are as follows:

| 286 287 288 |
|---|
| AGG ACC AAC |
| Arg-Asn-Asn |

Table 1 below sets out the codons and amino acid residues of the Leon strain and a mutant strain of poliovirus type 3, of Sabin strain poliovirus type 2 and of the Sabin and Mahoney strains of poliovirus type 1 in comparison to codons 286-290 for the Sabin strain of poliovirus type 3.

A preferred peptide according to the invention, suitable for use in vaccination against or diagnosis of a disease caused by type 3 poliovirus, is a tripeptide of formula (I) or pentapeptide of formula (II)

$$A_0\text{-}A_1\text{-}A_2 \qquad (I)$$

$$A_0\text{-}A_1\text{-}A_2\text{-}Leu\text{-}A_3 \qquad (II)$$

in which (i) $A_0$ is Arg, each of $A_1$ and $A_2$ is independently Asn or Gln and $A_3$ is Asp or Glu or (ii), with the others of $A_0$ to $A_3$ being as defined under (i), $A_0$ is Lys or $A_1$ or $A_2$ is Asp or Glu; or an antigenic equivalent thereof. Preferably, both $A_1$ and $A_2$ are Asn and $A_3$ is Asp. More preferably, $A_0$ is Arg.

A preferred peptide, suitable for use in vaccination against or diagnosis of a disease caused by type 2 poliovirus, is a tripeptide of formula (I) or pentapeptide of formula (II) in which $A_0$ is Lys, $A_1$ is Asp or Glu, $A_2$ is Gly and $A_3$ is Thr or Ser; or an antigenic equivalent thereof. More preferably, $A_1$ is Asp and $A_3$ is Thr.

A preferred peptide, suitable for use in vaccination against or diagnosis of a disease caused by type 1 poliovirus, is a tetrapeptide of formula (III) or a hexapeptide of formula (IV):

$$Lys\text{-}A_4\text{-}Gly\text{-}A_5 \qquad (III)$$

$$Lys\text{-}A_4\text{-}Gly\text{-}A_5\text{-}Leu\text{-}A_6 \qquad (IV)$$

in which $A_4$ is Asp or Glu, and each of $A_5$ and $A_6$ is independently Ser or Thr; or an antigenic equivalent thereof. More preferably, $A_4$ is Asp and $A_5$ and $A_6$ are both Thr.

The present invention also includes peptides longer than the basic tripeptide or pentapeptide, in the case of polioviruses types 2 and 3, or tetrapeptide or hexapeptide, in the case of poliovirus type 1. Further amino acids and/or peptides can be linked to one or both ends of the basic peptide chain. Preferably, 1, 2, 3 or 4 extra amino acid residues may be attached to the C-terminal of the basic peptide and/or 1, 2, 3 or 4 extra amino acid residues can be attached at the N-terminal of the basic peptide. Preferably, these additional amino acids correspond to those in a "natural" sequence. Thus, a longer peptide according to the invention may correspond to codons 282 to 292 in the RNA sequence coding for the VP1 capsid protein of poliovirus type 3 Sabin strain or equivalent codons of another poliovirus such as poliovirus type 1 or 2 Sabin strain. Such peptides in relation to the Sabin strains are:

(type 1) Gly-Val-Asp-Tyr-Lys-Asp-Gly-Thr-Leu-Thr-Pro-Leu (type 2) Gly-Val-Asp-Tyr-Lys-Asp-Gly-Leu-Thr-Pro-Leu (type 3) Gly-Val-Asp-Tyr-Arg-Asn-Asn-Leu-Asp-Pro-Leu The longer polypeptides may terminate in a Cys residue at one or both ends. Alternatively, the basic peptide chain itself or longer peptides containing this chain may be linked at one or both ends to a protein and/or some other carrier.

When, for example, the basic three or four amino acid sequence of a "natural" peptide or of an antigenic equivalent thereof is included in a longer peptide, the additional amino acids attached to the basic peptide preferably correspond to the amino acids linked to the "natural" peptide in the corresponding natural VP1 capsid protein. In type 3 Sabin poliovirus, the first N-terminal amino acid which may be added to the basic tripeptide is Tyr (coded for by UAU as can be seen from the Figure of the accompanying drawing). The first C-terminus amino acid which may be added in this instance is Leu (coded for by UUG). Appropriate further amino acids in this case can be determined from the Figure.

Larger compounds are such that the basic peptide sequence is positioned so as to be readily available to induce the appropriate immune response and, in particular, so that it is not "buried" in the interior of the molecule. Thus, for example, repeats of basic peptide may be linked together either by non-covalent or, preferably, covalent bonds. Where no appropriate amino acid is contained in the peptide sequence of the present invention, additional acids can be attached at either terminus for this purpose, in particular Cys which will enable covalent bonding through formation of a disulphide linkage.

Alternatively, a longer peptide may be formed into a loop by including groups which can link together at each terminus of the chain. A loop can of course be created by formation of an amide link between the N-terminus and C-terminus which can occur irrespective of the amino acids at those termini. Also, a longer peptide may comprise sequences for different types of poliovirus. Such a peptide would be useful as a vaccine for or in the diagnosis of two or all three types of poliovirus.

A peptide of the invention may comprise the basic peptide sequence linked to the sequence of a polypeptide according to GB-A-2 128 621. The polypeptides of GB-A-2 128 621 are hexapeptides coded for by codons 93-98 in the RNA sequence coding for the structural capsid protein VP1 of poliovirus type 3 Sabin strain or by equivalent codons of another enterovirus or are antigenic equivalents of such a hexapeptide. Preferably, the basic peptide sequence according to the present invention and the polypeptide according to GB-A-2 128 621 which are linked together are in respect of the same type, more preferably the same strain, of enterovirus.

A preferred hexapeptide according to GB-A-2 128 621, suitable for use as a vaccine for or in the diagnosis of type 3 poliovirus, has the formula (III):

$$A_{10}\text{-}A_{11}\text{-}A_{12}\text{-}A_{13}\text{-}A_{14}\text{-}A_{15} \qquad (III)$$

in which (A) $A_{10}$ is Glu, $A_{11}$ is Gln, $A_{12}$ is Pro, $A_{13}$ is Thr, $A_{14}$ is Thr and $A_{15}$ is Arg, or (B) with the remainder of $A_{10}$ to $A_{15}$ being as defined under (A), (a) $A_{10}$ is Gly or (b) $A_{13}$ is Ile, Ser, Ala or Asn or (c) $A_{14}$ is Asn, Ser or Ile or (d) $A_{15}$ is Gln, Trp or Gly or (e) $A_{13}$ is Ile and $A_{14}$ is Asn or Ala. This hexapeptide can therefore be linked to the preferred type 3 poliovirus tripeptide of formula (I) above.

A preferred hexapeptide according to GB-A-2 128 621, suitable for use as a vaccine for or in the diagnosis of type 2 poliovirus, has the formula (III) in which $A_{10}$ is Asp, $A_{11}$ is Ala, $A_{12}$ is Pro, $A_{13}$ is Thr, $A_{14}$ is Lys and $A_{15}$ is Arg. This hexapeptide may therefore be linked to the preferred type 2 poliovirus tripeptide of formula (I) above.

A preferred hexapeptide according to GB-A-2 128 621, suitable for use as a vaccine for or in the diagnosis of type 1 poliovirus, has the formula (III) in which $A_{11}$ is Ala, $A_{12}$ is Ser, $A_{13}$ is Thr, $A_{15}$ is Asn and either (A) $A_{10}$ is Ser and $A_{14}$ is Lys or (B) $A_{10}$ is Pro and $A_{14}$ is Thr. This hexapeptide may therefore be linked to the preferred type 1 poliovirus tripeptide of formula (II) above.

The hexapeptides of GB-A-2 128 621 can be built up into longer polypeptides, and these longer polypeptides may too be linked to peptides according to the present invention. For example a preferred type 3 poliovirus octapeptide according to GB-A-2 128 621 has the formula (IV):

$$A_{10}\text{-}A_{11}\text{-}A_{12}\text{-}A_{13}\text{-}A_{14}\text{-}A_{15}\text{-}A_{16}\text{-}A_{17} \qquad (IV)$$

in which $A_{10}$ is Glu, $A_{14}$ is Thr or Ser and $A_{15}$ is Arg. More preferably, (A) $A_{10}$ is Glu, $A_{11}$ is Gln, $A_{12}$ is Pro, $A_{13}$ is Thr, $A_{14}$ is Thr, $A_{15}$ is Arg, $A_{16}$ is Ala and $A_{17}$ is Gln, or (B) with the others of $A_{10}$ to $A_{17}$ being as defined in (A), (a) $A_{10}$ is Gly, or
(b) $A_{13}$ is Ile, Ala or Asn, or
(c) $A_{14}$ is Asn, Ser or Ile, or
(d) $A_{15}$ is Gln or Trp, or
(e) $A_{16}$ is Thr or Val, or
(f) $A_{17}$ is Leu, Pro, Arg or His; or further
(g) $A_{13}$ is Ser, Ile or Asn and $A_{16}$ is Thr, or
(h) $A_{13}$ is Ile, $A_{14}$ is Asn or Ala and $A_{16}$ is Thr.

A preferred type 2 poliovirus octopeptide has the formula (IV) in which: $A_{10}$ is Asp, $A_{11}$ is Ala, $A_{12}$ is Pro, $A_{13}$ is Thr, $A_{14}$ is Lys, $A_{15}$ is Arg, $A_{16}$ is Ala and $A_{17}$ is Ser.

A preferred type 1 poliovirus octopeptide has the formula (IV) in which: $A_{11}$ is Ala, $A_{12}$ is Ser, $A_{13}$ is Thr, $A_{15}$ is Asn, $A_{16}$ is Lys, $A_{17}$ is Asp and either (A) $A_{10}$ is Ser and $A_{14}$ is Lys or (B) $A_{10}$ is Pro and $A_{14}$ is Thr.

Further amino acids and/or peptides can be linked to one or both ends of these eight amino acid polypeptide chains according to GB-A-2 128 621. For example, a dodecapeptide or an octadecapeptide may be formed respectively by bonding:

(poliovirus type 3) Glu-Val-Asp-Asn-,
(poliovirus type 2) Glu-Val-Asp-Asn-,
(poliovirus type 1) Thr-Val-Asp-Asn-, to residue $A_{10}$ of formula (IV), or
(poliovirus type 3) Ala-Ile-Ile-Glu-Val-Asp-Asn- and -Lys-Leu-Phe,
(poliovirus type 2) Ala-Ile-Ile-Glu-Val-Asp-Asn- and -Arg-Leu-Phe, or (poliovirus type 1) Ala-Ile-Ile-Thr-Val-Asp-Asn- (when $A_{10}$ is Ser and $A_{14}$ is Lys) or Thr-Thr-Met-Thr-Val-Asp-Asn- (when $A_{10}$ is Pro and $A_{14}$ is Thr) and -Lys-Leu-Phe, to residues $A_{10}$ and $A_{17}$ of formula (IV).

The basic peptide sequence according to the present invention may be linked to a polypeptide according to GB-A-2 128 621 in any suitable manner. They may be linked directly to each other or by one or more amino acid residues or by a disulphide bridge between Cys residues attached to each. Not only may peptides of the same poliovirus type be linked together but also peptides of different types may be linked so as to form a single peptide useful as a vaccine for or in the diagnosis of two or all three types of poliovirus.

A peptide of the invention may also comprise the basic peptide sequence linked to another peptide comprising residues 58 and 59, for example residues 58 to 61, of the VP3 capsid protein of the same type, preferably of the same strain, of enterovirus, in particular poliovirus, as that to which the basic sequence corresponds. For poliovirus type 3, the other peptide may also comprise VP3 residues 77 and 79. It is believed that for poliovirus type 3 the pentapeptide coded for by codons 286–290 in the VP1 and VP3 residues 58,59,77 and 79, which are thought to constitute a subsidiary antigenic site, form a single operationally distinct antigenic site.

Thus, the invention provides a peptide suitable for use in vaccination against or diagnosis of a disease caused by type 3 poliovirus, which comprises a type 3 pentapeptide of formula (II) above linked to a VP3 peptide of formula (V) or (VI):

$A_7$-$A_8$-$A_9$-Lys  (V)

$A_7$-$A_8$-$A_9$-Lys ... $A_{10}$ ... $A_{11}$  (VI)

in which (i) each of $A_7$ and $A_{10}$ is independently Glu or Asp, each of $A_8$, $A_9$ and $A_{11}$ is independently Thr or Ser and $A_{10}$ and $A_{11}$ are linked to the Lys residue and $A_{10}$ respectively either directly or through intervening amino acid residues or (ii), with the others of $A_7$ to $A_{11}$ being as defined under (i), $A_7$ is Asn or Gln or $A_8$ is Arg, Asn or Gln. The peptide of formula (VI) may therefore correspond to VP3 amino acid residues 58 through to 79 of, for example, Sabin or Leon strain type 3 poliovirus. Preferably, $A_7$ is Glu, $A_8$ and $A_{11}$ are both Ser, $A_9$ is Thr and $A_{10}$ is Asp.

The invention also provides a peptide suitable for use in vaccination against or diagnosis of a disease caused by type 2 poliovirus, which comprises a type 2 pentapeptide of formula (II) above linked to a VP3 peptide of formula (VII) or (VIII):

$A_{12}$-$A_{13}$-$A_{14}$-Arg  (VII)

$A_{12}$-$A_{13}$-$A_{14}$-Arg ... His ... $A_{15}$  (VIII)

in which each of $A_{12}$ and $A_{13}$ is independently Thr or Ser, $A_{14}$ is Gln or Asn, $A_{15}$ is Asp or Glu and the His residue and $A_{15}$ are linked to the Arg residue and the His residue respectively either directly or through intervening amino acid residues. The peptide of formula (VIII) may therefore correspond to VP3 amino acid residues 58 through to 79 of, for example, Sabin strain type 2 poliovirus. Preferably, $A_{12}$ is Thr, $A_{13}$ is Ser, $A_{14}$ is Gln and $A_{15}$ is Asp.

The invention further provides a peptide suitable for use in vaccination against or diagnosis of a disease caused by type 1 poliovirus, which comprise a type 1 hexapeptide of formula (IV) above linked to a VP3 peptide of formula (IX) or (X):

$A_{16}$-Ala-Lys-Lys  (IX)

$A_{16}$-Ala-Lys-Lys ... His ... $A_{17}$  (X)

in which $A_{16}$ is Thr or Ser, $A_{17}$ is Asp or Glu and the His residue and $A_{17}$ are linked to the Lys residue shown adjacent to the His residue in formula (X) and the His residue respectively either directly or through intervening amino acid residues. The peptide of formula (X) may therefore correspond to VP3 amino acid residues 58 through to 79 of, for example, Sabin or Mahoney strain type 1 poliovirus. Preferably, $A_{16}$ is Ser and $A_{17}$ is Asp. The hexapeptide of formula (IV) may be linked to the peptide of formula (IX) or (X), and the type 3 and 2 pentapeptides of formula (II) may be linked to the peptide of formula (V) or (VI) and the peptide of formula (VII) or (VIII) respectively in the same manner as the basic peptide sequence according to the invention may be linked to a polypeptide according to GB-A-2 128 621.

A peptide of the present invention, if not itself immunogenically active, may be linked to a carrier in order to create a conjugate which will be immunogenically active. The carrier in that case may be a protein such as bovine serum albumin, thyroglobulin, ovalbumin or keyhole limpet hemocyanin, or palmitic acid. For immunization of humans, the carrier must be a physiologically acceptable carrier acceptable to humans and safe. Preferably however, the peptide is linked to tetanus toxoid and/or diptheria toxoid thus providing both an immunogen and a multivalent vaccine at the same time. Alternatively, the peptide may be chemically bonded to inert carriers where they can be used to assay and/or isolate by affinity chromatography antibodies to the appropriate virus. Examples of such inert carriers are dextrans e.g. sepharose.

The present invention also provides a process for the preparation of a peptide of the invention, which process comprises identifying either (a) the codons in the RNA sequence coding for the structural capsid protein VP1 of an enterovirus which are or which are equivalent to codons 286 to 288, preferably codons 286 to 290, for a poliovirus type 3 Sabin strain or (b) the corresponding codons in a DNA sequence corresponding to said RNA sequence; and producing a synthetic peptide comprising the peptide sequence corresponding to the codons thus identified, or an antigenic equivalent thereof.

A peptide of the invention may be produced by chemical synthesis, for example by one of the generally known methods. In these methods, the peptide is usually built up either from the N-terminus or, more usually, the C-terminus using either single amino acids or preformed peptides containing two or more amino acid residues. Particular techniques for synthesising peptides include the classical methods where the peptides of increasing size are usually isolated before each amino acid or preformed peptide addition. Alternatively, solid phase peptide synthesis may be employed where the peptide is built up attached usually to a resin e.g. a Merrifield resin. In these syntheses, groups on the amino acids will generally be in protected form using standard protecting groups such as t-butoxycarbonyl. If necessary, these protecting groups are conveniently cleaved once the synthesis is complete, though they may be retained where they do not affect the ability of the compound including the peptide to provoke an appropriate immune response. Other modifications of the peptide may either be introduced during the synthesis or at the end of it.

A still further possible method for producing the peptides of the invention is by employing the techniques of genetic engineering whereby a DNA sequence coding for the peptide is introduced into a plasmid which itself is introduced into an organism e.g. a bacterium, which can be induced to make the peptide in recoverable form. The present invention thus not only covers the peptide, but also a DNA or RNA sequence coding for the peptide which can be used in such a synthesis. However, in view of the small number of amino acids in the peptide chain of the invention, the most appropriate methods of production are the synthetic methods for building up the chains described above.

The peptides of the present invention have a particular application in vaccinating patients against diseases caused by enteroviruses, in particular polioviruses. Vaccination is achieved by administering to a patient an effective amount of a peptide of the invention, either as such or linked to a carrier. Typically, from 100 µg to 1 mg of the peptide is administered intramuscularly to a human.

When used for this purpose, the material must be such, particularly of such a size, that it produces an immune reaction. The peptide is usually therefore coupled to an immunogenically active carrier such as the proteins mentioned hereinbefore or be in the form of a longer peptide including the peptide sequence, which may be achieved by linking the peptide to a synthetic polypeptide such as poly-lys.

The vaccines may include not just one peptide in accordance with the present invention, but two or more. By including several different peptides, for example one for each of the three different types of poliovirus, a patient may be vaccinated against all three types of poliovirus and the vaccine can also take account of variations in the peptide between different viruses of the same type.

Further, a peptide according to the present invention may therefore be administered with a polypeptide according to GB-A-2 128 621 and/or a VP3 peptide as described above. The peptides may be mixed together or administered separately over a period of time in any order. Preferably, peptides in respect of the same type, more preferably the same strain, of enterovirus are administered. Preferred polypeptides according to GB-A-2 128 621 and preferred VP3 peptides which may be administered simultaneously with or separately from a peptide according to the present invention are those mentioned above. Alternatively, a polypeptide according to GB-A-2 128 621 and/or a VP3 peptide may be linked to the same carrier as a polypeptide of the present invention.

It is also preferred to formulate vaccine compositions as physical mixtures which include other antigens particularly those commonly used in infant vaccines, such as tetanus, diphtheria and whooping cough. However, as indicated before, such antigens may, if desired, be linked chemically to the peptide of the invention in order to render it immunogenic.

Although the peptides of the present invention, when in immunogenic form, can act as vaccines to protect a patient by inducing the production of the appropriate antibodies, it is possible that, in addition, the peptide may have a chemotherapeutic effect. Thus it is believed that the same peptide sequence which can evoke the production of antibodies may be the sequence in the viral capsid protein which enables the virus to attach itself to a cell within a patient and thereby cause the infection. Thus the peptide of the present invention may have a competitive effect and, by occupying the appropriate cell receptor sites, prevent the virus itself from infecting the patient. Generally, immunogens comprising the peptides of the present invention will be administered by injection which will usually be intramuscular but can be by routes, such as intraperitoneally or subcutaneously.

The peptides of the present invention can also be used to prime the immune system of a patient to exhibit an enhanced response to vaccination against diseases caused by enteroviruses. An effective amount, typically 100 µg to 1 mg, of a peptide of the invention can be administered to a patient and, after a suitable amount of time has elapsed, the patient can be vaccinated against a disease caused by a corresponding enterovirus in the conventional manner. Less material, both of the peptide of the invention and of that required for the conventional vaccination, may be needed and fewer challenges may be required to achieve effective vaccination.

The present invention also provides a pharmaceutical composition which includes a peptide of the present invention as active ingredient, together with a pharmaceutically acceptable carrier or diluent. The actual form of the peptide in this composition, i.e. whether it is linked to another compound or not, will depend upon the use to which the composition is to be put. The composition may be presented as a vaccine, for example comprising an effective amount of the peptide in a suitable diluent such as Freunds Complete Adjuvant (FCA) or physiologically acceptable saline.

An alternative use for the peptides of the present invention is in the diagnosis of infection by enteroviruses. This diagnosis may be carried out by the detection of the presence or absence of antibody to the appropriate virus in the patient. For this purpose, the peptides are usually bonded to inert carriers as mentioned hereinbefore and, in such form, they can also be used as an affinity chromatography medium in the isolation of antibodies to the virus. The peptide of the invention may therefore form a component of a test kit, suitable for use in determining antibody against an enterovirus, which kit also includes means for determining antibody bound to the peptide. Any suitable immunoassay system, for example radioimmunoassay system, may be used to determine the antibody.

The following Examples illustrate the invention.

Example 1

Identification of the antigenic sitecoded for by codons 286–288 in the RNA sequence coding for the VP1 capsid protein of poliovirus type 3 Sabin strain Mutants which were resistant to neutralization by specific monoclonal antibodies were isolated by plaque formation by antibody-treated virus under an agar overlay containing antibody (Minor et al 1983). They were isolated from the type 3 poliovirus strain P3 Leon-/USA/1937 (Minor et al 1983, Evans et al 1983) and its attenuated derivative the Sabin vaccine strain. The mutants were characterized by their susceptibility to neutralization by a panel of twelve monoclonal antibodies as shown in Table 2 below. Mutants obtained from a total of 213 plaques derived from P3/Leon/37 virus could be classified into 16 distinct groups on the baisis of the pattern of their neutralization. Similarly fifteen distinct groups of mutants were selected from the Sabin vaccine strain from a total of 129 plaques.

Evidence for a second, independent antigenic site was obtained using a highly strain-specific monoclonal antibody, 138, which neutralizes the Sabin type 3 vaccine virus or most strains derived from it, but not P3/Leon/37 or other strains (Ferguson et al 1982). All mutants of the Sabin strain which were resistant to the twelve antibodies which selected mutants with substitutions in the first site (see GB-A-2 128 621), were found to be still sensitive to antibody 138, while all mutants selected for resistance to antibody 138 were fully sensitive to these site 1 antibodies. Antibody 138 was therefore thought to be directed against an independently mutable site, distinct from the first site. This second site was identified as follows.

Nucleotide sequencing studies (Stanway et al 1983, 1984) indicate that there are only two predicted amino acid differences between Leon $12a_1b$ (the Sabin strain) and P3/Leon USA 1937 in the structural portion of the genome, one in the region coding for protein VP3, the other at codon 286 from the 5' end of the region coding for VP1, which is a lysine in P3/Leon/37 and an arginine in the Sabin vaccine strain. A recombinant plasmid was prepared from whole cloned cDNA copies of the genomes of Sabin type 3 vaccine virus and P3/Leon/1937 such that the recombinant genome contained the VP3 region of the Sabin strain and the VP1 of Leon (G Westrop, unpublished). Virus was recovered by transfection of cells with this plasmid (Racaniello and Baltimore 1981) and characterized by partial sequencing of the genome in the regions coding for VP1 and VP3. This recombinant virus failed to react with antibody 138, suggesting that the specific site did not involve VP3 of the Sabin strain, but included the amino acid at position 286 from the N terminus of VP1.

Mutants resistant to 138 isolated from Sabin virus proved to have a base substitution in the adjacent codon (287) leading to the substitution of an aspartate residue for asparagine.

Additionally, a series of isolates was obtained from a hypogammaglobulinaemic vaccine (222f) who excreted a vaccine derived type 3 poliovirus for a prolonged period after administration of a monovalent type 3 Sabin vaccine (MacCallum 1971). Six of these strains proved to be different from each other on the basis of T1 oliogonucleotide maps of their RNA, but all failed to react with antibody 138 (P Minor unpublished). Sequencing studies revealed that the amino acid at codon 288 from the N-terminus of VP1 was aspartate for all six excreted strains and asparagine for the parental Sabin vaccine virus.

The findings with recombinant virus, mutant virus and excreted strains strongly imply that antibody 138 recognises a strain specific antigenic site encompassing codons 286–288 from the N-terminus of VP1.

Example 2

Identification of the antigenic site coded for by codons 286–290 in the RNA sequence coding for the VP1 capsid protein, and a subsidiary antigenic site coded for by codons including 58,59,77 and 79 in the RNA sequence coding for the VP3 capsid protein, of poliovirus type 3 Sabin strain Monoclonal antibodies were prepared by the fusion of splenocytes from immunised Balb/C mice with my-eloma cells as described (Ferguson et al 1984). The mice were immunised with antigenically abnormal virus, either an antigenically drifted strain (P3/23127/Finland/84) implicated in an outbreak of poliomyelitis in Finland (Lenikki et al 1985) or poliovirus type 3 Sabin strain which had been treated with trypsin as described (Fricks et al 1985). Hybridoma supernatants were screened using a modified single radical diffusion assay (antigen blocking test) and monoclonal antibodies were generally used as ascites prepared in syngeneic mice (Ferguson et al 1984). Immunisation schedules and other protocols were similar in all fusions.

Monoclonal antibodies generated from animals immunised with both types of virus were able to neutralise both untreated virus and all mutants having substitution within the principal antigenic site, the region in the VP1 capsid protein from amino acids 89 to 100. Mutants were selected with four of these antibodies as follows. Antigenic variants were selected by plaque formation on Hep2c cells by virus treated with antibody under an agar overlay containing the antibody as described (Minor et al 1983). Putative mutants were subject to two cycles of selection, and small working pools grown up from the secondary plaque plugs.

The antigenic patterns of reaction of the mutants picked are shown in Table 3, together with two mutants which have been previously described. Mutant 1 had an amino acid substitution in VP1 at position 98, where a glycine residue was found instead of an arginine. Mutant 2 had a mutation in VP1 at position 287, where an aspartate residue was found in place of an sparagine. The thirteen mutants fell into three distinct non overlapping groups, implying the existence of three independent antigenic sites.

The genomic RNA of mutants 3 to 13 was sequenced by primer extension, through five regions corresponding to areas containing antigenically significant mutations in type 1 or type 3 poliovirus. These included regions coding for residues 89 to 100, 220 to 222 and 286 to 290 of VP1, residues 50 to 80 of VP3 and residues 160 to 180 of VP2. The results are presented in Table 4. Mutants 2 to 8 had single base substitutions resulting in predicted amino acid changes in VP1 at residues 287 and 290, and in VP3 at residues 58, 59, 77 and 79. It was notable that the reactions of antibodies 1023, 840, 251, 557, 1084 and 1007 were affected both by mutations within VP3 at residues 58 and 59 and by mutations within VP1 at residues 287 and 290. It is believed that the second antigenic site comprising residues 286 to 290 of VP1 and the subsidiary antigenic site comprising residues 58,59,77 and 79 form a single operationally distinct antigenic site.

Example 3

Synthesis of Cys-Glu-Val-Asp-Asn-Glu-
Gln-Pro-Thr-Thr-Arg-Ala-Gln-Lys-Leu-Phe-Ala-Met-
Gly-Val-Asp-
Tyr-Arg-Asn-Asn-Leu-Asp-Pro-Leu-Cys (Peptide 1)
and
Cys-Gly-Val-Asp-Tyr-Arq-Asn-Asn-Leu-Asp-Pro-
Leu-Cys (Peptide 2)

The required peptides were synthesised by the Fmoc-polyamide mode of solid phase peptide synthesis (Brown et al 1983 and references cited therein). The general protocol was as follows:

Polydimethylacrylamide gel resin (a copolymer of dimethylacrylamide-ethylenebisacrylamide-acryloylsarcosine methyl ester) containing 0.3 milliquivalents of sarcosine per gram resin, was treated with ethylenediamine overnight. After thorough washing, the acid labile linkage agent, 4-hydroxymethylphenoxyacetic acid, was added as its symmetrical anhydride. After thorough washing this afforded the low loading acid labile resin that was used to prepare the peptides under discussion.

Fmoc-amino acids were coupled (in a twelve fold excess) as their preformed symmetrical anhydrides: the Fmoc-amino acid (2 equiv) was dissolved in dichloromethane with a few drops of N,N-dimethylformamide (DMF) if required to aid dissolution. N,N-Dichlorohexylcarbodiimide (DCC) (1 equiv) was added and the mixture stirred at room temperature for 10 minutes. The precipitated N,N-dicyclohexylurea (DCU) was filtered off, the filtrate evaporated to dryness and the residue dissolved in DMF. This solution was added to the deprotected and washed resin and the coupling reaction allowed to proceed.

Asparagine and glutamine residues were added as follows: 1-hydroxybenzotriazole (1 equiv) and DCC (1 equiv) were dissolved in DMF at 0° C. After stirring for ten minutes at 0° C. a solution of Fmoc-asparagine (or glutamine) (1 equiv) in DMF was added This mixture was stirred for a further ten minutes at 0° C. and then the entire mixture added to the resin and coupling allowed to proceed.

A typical synthetic cycle was as follows:

| Reagent | Duration | Operation |
|---|---|---|
| DMF | 5 × 1 min | Wash |
| 20% Piperidine/DMF | 1 × 3 + 1 × 7 min | Deprotection |
| DMF | 10 × 1 min | Wash |
| Preformed symmetrical anhydride or active ester | 60–120 min | Coupling |
| DMF | 5 × 1 min | Wash |

The completeness of coupling at each stage was monitored using ninhydrin and trimethylbenzenesulphonic acid test reagents.

The coupling of the first residue to the derivatised resin was carried out in the presence of N,N-dimethylaminopyridine (DMAP) (0.1 equiv)

As the C-terminal dodecapeptide sequence was common to both peptides, the synthesis was carried out on twice the scale, half being used to continue the first peptide and cysteine being added to the other half to give the second peptide.

The quantities used were as follows:

Acid Labile Resin (0.1 g; 0.3 mequiv g$^{-1}$); for each cycle, Fmoc-amino acid (3.6 mmol) and DCC (0.38 g; 1.8 mmol); for the first cycle, DMAP (0.022 g; 0.18 mmol); and, for asparagine and glutamine residues HOBT (0.24 g; 1.8 mmol). The cycles were carried out on the following basis:

| Fmoc-amino acid-OH | Quantities | Coupling Time |
|---|---|---|
| Fmoc-Cys(Trt)-OH | 2.10 g; 3.6 mmol | 1 hour |
| Fmoc-Leu-OH | 1.28 g; 3.6 mmol | 1 hour |
| Fmoc-Pro-OH | 1.22 g; 3.6 mmol | 1 hour |
| Fmoc-Asp(OBu$^t$)-OH | 1.48 g; 3.6 mmol | 1 hour |
| Fmoc-Leu-OH | 1.28 g; 3.6 mmol | 1 hour |
| Fmoc-Asn-OH | 0.64 g; 1.8 mmol | 1 hour |
| Fmoc-Asn-OH | 0.64 g; 1.8 mmol | 3 hour |
| Fmoc-Arg(Mtr)-OH | 2.20 g; 3.6 mmol | 1 hour |
| Fmoc-Tyr(Bu$^t$)-OH | 1.64 g; 3.6 mmol | 1 hour |
| Fmos-Asp(OBu$^t$)-OH | 1.48 g; 3.6 mmol | 1 hour |
| Fmoc-Val-OH | 1.22 g; 3.6 mmol | 1 hour |
| Fmoc-Gly-OH | 1.08 g; 3.6 mmol | 1 hour |

Resin split in half after deprotection, to half was added:

| | | |
|---|---|---|
| Boc-Cys(Trt)-OH | 0.83 g; 1.8 mmol | 1 hour | giving the second peptide.

To the other half of the resin was added:

| Fmoc-amino acid-OH | Quantities | Coupling Time |
|---|---|---|
| Fmoc-Met-OH | 0.67 g; 1.8 mmol | 1 hour |
| Fmoc-Ala-OH | 0.56 g; 1.8 mmol | 1 hour |
| Fmoc-Phe-OH | 0.74 g; 1.8 mmol | 1 hour |
| Fmoc-Leu-OH | 0.64 g; 1.8 mmol | 1 hour |
| Fmoc-Lys(Boc)-OH | 0.84 g; 1.8 mmol | 1 hour |
| Fmoc-Gln-OH | 0.33 g; 0.9 mmol | 1 hour & 2 hours |
| Fmoc-Ala-OH | 0.56 g; 1.8 mmol | 1 hour |
| Fmoc-Arg(Mtr)-OH | 1.10 g; 1.8 mmol | 1 hour |
| Fmoc-Thr(Bu$^t$)-OH | 0.72 g; 1.8 mmol | 1 hour |
| Fmoc-Thr(Bu$^t$)-OH | 0.72 g; 1.8 mmol | 1 hour |
| Fmoc-Pro-OH | 0.61 g; 1.8 mmol | 1 hour |
| Fmoc-Gln-OH | 0.33 g; 0.9 mmol | 5 hours |
| Fmoc-Glu(OBu$^t$)-OH | 0.77 g; 1.8 mmol | 1 hour |
| Fmoc-Asn-OH | 0.32 g; 0.9 mmol | 1½ hours |
| Fmoc-Asp(OBu$^t$)-OH | 0.74 g; 1.8 mmol | 1 hour |
| Fmoc-Val-OH | 0.61 g; 1.8 mmol | 1 hour |
| Fmoc-Glu(OBu$^t$)-OH | 0.77 g; 1.8 mmol | 1 hour |
| Boc-Cys(Trt)-OH | 0.83 g; 1.8 mmol | 1 hour |

After washing both peptide resins were shrunk by washing with dichloromethane and diethyl ether.

Peptide 1

The peptide was cleaved from the resin and the side chain protecting groups were removed by treating the peptide resin with 95% trifluoroacetic acid (TFA)/5% ethane dithion (EDT) (3×1 hour). After filtration, evaporation of each fragment afforded a residue which on trituration with diethyl ether afforded three white solids (104 mg, 80 mg and 41 mg). Hplc (μBondpak C$_{18}$; linear gradient 5–95% 0.1% TFA/CH$_3$CN - 0.1% TFA/H$_2$O over 20 minutes) showed the product to consist of four major compounds, i.e. Mtr protecting groups still present. The Mtr (4-methoxy-2,3,6-trimethylbenzenesulphonyl) group used for the protection of the arginine side chain is cleaved considerably more slowly than the t-butyl based side chain protecting groups used for other functional residues and, therefore, extended treatment with trifluoroacetic acid was necessary to facilitate its removal. The three fractions were therefore combined and re-treated with TFA for a further five hours. Hplc showed one major peak and several smaller ones. The combined materials were dissolved in 10% acetic acid and then subjected to exclusion chromatography on Sephadex G-25 Superfine eluted with 10% acetic acid. The eluate was monitored at 254 nm and fractions corresponding to the required compound were combined and lyophilised affording the product as a white fluffy solid (130 mg). This compound did not give a molecular ion when subjected to fast atom bombardment mass spectrometry.

Peptide 2

The peptide was cleaved from the resin by treating with 95% TFA/5% EDT (3×1 hour). This afforded three white solids (70 mg, 61 mg and 42 mg). Hplc (same conditions as above) showed two major peaks again indicating Mtr groups present. The three fractions were combined and re-treated with TFA to give a white solid (149 mg). Hplc showed the product to be essentially homogeneous. FAB-mass spectrometry gave a sharp molecular ion at 1481, this being consistent with a molecular weight of 1480.

Example 4

Preparation of Cys-Ile-Pro-Phe-Asp-Leu-Ser-Ala-Thr-Lys-Lys-Asn-Thr-Met-Glu-Met-Tyr-Cys (Peptide 3) and
Cys-Ile-Pro-Leu-Asn-Leu-Glu-Ser-Thr-Lys-Arg-Asn-Thr-Met-Asp -Met-Tyr-Cys (Peptide 4)

These two peptides comprise amino acid residues 58 to 61 of the VP3 capsid protein of type 1 Sabin poliovirus (Peptide 3) and type 3 Sabin poliovirus (Peptide 4). Both peptides are composed of residues 53 to 68 with Cys residues at each terminus. The peptides were synthesised according to the procedure of Example 3. Hplc showed each product to be essentially homogeneous FAB-mass spectrometry gave a sharp molecular ion at 2097 for Peptide 3, this being consistent with a molecular weight of 2096, and at 2134 for Peptide 4, this being consistent with a molecular weight of 2133.

Example 5

Measurement of Specific Antibody Responses

The specific antibody responses of laboratory rabbits to peptides 1 and 2 were measured in respect to:
1. antibody to uncoupled peptide (1 or 2) detected by enzyme-linked immunoabsorbent assay (ELISA), and
2. antibody to polioviruses of types 1, 2 and 3 as detected by antigen blocking assays against poliovirus C antigen measured in single-radial-diffusion (SRD) tests in gels.

Coupling of peptide of bovine thyroglobulin 1 ml of 0.1M sodium phosphate buffer pH 7.5 was added to a glass vial containing 30 mg of bovine thyroglobulin (BTG, Sigma) or 30 mg of keyhole limpet haemocyanin. The dissolved material was transferred with 1 ml sodium phosphate buffer washing to a second vial containing 10 mg of peptide (1 or 2) to give a final volume of 2 ml peptide-BTG solution. The vial was wrapped in aluminium foil to exclude light. A solution of 2% glutaraldehyde was made in 0.1M sodium phosphate buffer pH 7.5 and 200 μl, added to the peptide-BTG solution in four lots of 50 μl, shaking between additions, and then left for 1 hour at room temperature with intermittent shaking. The solution was then dialysed against one liter of phosphate buffered saline (PBS) at 4° overnight, and then against 1 liter of fresh PBS for a further eight hours. Coupled peptide was stored at −70° C. until required.

Coupled oligopeptides used for immunization of experimental animals

Synthetic oligopeptides 1 and 2 were conjugated separately to bovine thyrogobulin (BTG) as described above. The preparations used for immunization contained 500 ug/ml of peptide 1 or 2 and 1500 ug/ml of BTG suspended in phosphate buffered saline (pH 7.2).

Immunization schedule for experimental animals

Young (5-6 months of age) healthy rabbits were injected intramuscularly with an initial dose of 0.5 ml (500 ug) coupled peptide mixed with an equal volume of Freunds complete adjuvant (FCA, Bacto) and subsequently injected with booster doses (0.5 ml) 500 ug coupled peptide according to the following schedule. Serum samples for analysis were collected at intervals up to 76 days after the first injection.

| | | |
|---|---|---|
| Day 0 | 0.5 ml coupled peptide + FCA | serum sample |
| Day 20 | | serum sample |
| Day 24 | 0.5 ml coupled peptide + FCA | — |
| Day 28 | | serum sample |
| Day 41 | | serum sample |
| Day 44 | 0.5 ml coupled peptide | — |
| Day 55 | | serum sample |
| Day 76 | | serum sample |

Enzyme immunoassays (ELISA) for antibody to oligopeptide

Enzyme immunoassays were carried out to investigate the immune response of the rabbit to the peptide. Rabbit sera were examined for antibody which bound to oligopeptide linked to polyvinyl plates by glutaraldehyde. The bound antibody was detected by the addition of anti rabbit antibodies which were coupled to biotin followed by streptavidin biotinylated horse radish peroxidase complexes. On addition of substrate for the horseradish peroxidase (5-aminosalicylic acid) a colorimetric change takes place, the intensity of which is proportion to the amount of antibody bound to peptide.

Ninety-six well Microelisa plates (Dynatech) were coated with oligopeptide (10 μg/ml) After incubation overnight at 4° centigrade plates were washed ×5 with PBS containing 0.5% Tween 20 (Koch-Light Laboratories, Colnbrook, Berks) Dilutions of rabbit sera in PBS were added to wells and incubated for 2 hours at 37° C. Plates were washed ×5 with phosphate buffered saline containing 0.5% Tween 20 and donkey anti rabbit Ig linked to Biotin (Amersham International) diluted in PBS added. After 1 hour at 37 degrees centigrade the biotinylated antibody was removed, the plates washed ×5 with phosphate buffered saline containing Tween 20. Streptavidin biotinylated horseradish peroxidase complexes were added and the plates incubated at 37° C. for 30 minutes. The plates were washed ×3 in PBS containing 0.5% Tween 20 and ×2 with PBS and the substrate, 5-aminosalicylic acid (80 μg in 100 ml PBS was added to each well. The plates were incubated at 37 degrees centigrade until colour developed. Optical density was read on a Titertek multiscan set at 492 nm. The machine was 'blanked' using substrate and serum dilutions considered positive if the optical density was greater than that of 1:100 dilution of normal rabbit serum collected from the animal prior to immunization of the peptide.

Antigen blocking assays for antibody to poliovirus antigen employing single radial diffusion (SRD) in gel The rabbit sera were tested in SRD antigen-blocking tests to determine their reactivities with C antigen of poliovirus type 1 or 3. The method used was a modification of the autoradiographic SRD method of Schild et al (1980) as described elsewhere (Ferguson et al 1982). Briefly, [35S]-methionine labelled 80S 'C' peaks of poliovirus antigen from sucrose gradients were mixed with the test monoclonal antibody before adding to wells in agarose gels containing low concentrations of hyperimmune anti-poliovirus type 3 serum. Diffusion or radiolabelled antigen in the gel after 24-48 h was detected by autoradiography. Test antibody which reacts with 'C' antigen inhibits its diffusion into the gel compared with control antigen treated with phosphate buffered saline alone. The antigen blocking titres are assessed as the dilution of serum which significantly reduces the zone size in comparison with zones produced with control antigen mixed with phosphate buffered saline.

RESULTS

Induction of antibody to homologous peptide

The titres of antibody to peptide 2 determined by ELISA assay are shown in Table 5 for representative animals. Twenty one days following the initial immunization with peptide all animals had readily demonstrable antibody to homologous peptide. The titres had increased by day 41 and in later serum samples following booster doses of the oligopeptides. No anti-peptide antibody was detected in prebleeds from any animal. Table 6 shows ELISA titres to peptide 1. This peptide is peptide S10a of GB-A-2 128 621 plus peptide 2 linked together and the titres of antibody reached with each peptide are also given.

Induction of antibody to poliovirus (a) antigen blocking antibody

Antibody specific for empty virions (C antigen) may be detected by antigen blocking assays employing the single radial diffusion test (Schild et al 1980, Ferguson et al 1982). This method was applied to sera obtained from animals immunized with peptides 1 and 2 coupled to BTG.

Table 7 shows the induction of blocking antibodies to poliovirus type 3 C antigen in rabbits injected with peptide 2. Antibody first appeared between day 17 and 31 in 3 out of 4 animals. Antisera from animals immunised with peptide 2 were tested against viruses with mutations in the VP1 antigenic sites both of the present invention and of GB-A-2 128 621. The results are shown in Table 8.

Table 9 shows the induction of blocking antibodies to poliovirus type 3 C antigen in rabbits injected with peptide 1.

Reference

Brown et al 1983, J. Chem. Soc. Perkin Trans. I, 1161 et seq

Evans et al, 1983, Critical role of an eight amino acid sequence of VP1 in neutralization of poliovirus type 3, Nature 304, 459-462.

Ferguson et al 1982, Monoclonal antibodies specific for the Sabin vaccine strain of poliovirus, Lancet II 122-124.

Ferguson et al 1984, Neutralisation epitopes on poliovirus type 3 particles: an analysis using monoclonal antibodies, J. Gen.Virol. 65, 197-201.

Fricks et al 1985, Trypsin sensitivity of the Sabin strain of type 1 poliovirus cleavage sites in virions and related particles, J. Virol. 54, 856 et seq Leinikki et al 1985, Paralytic poliomyelitis in Finland, Lancet II 507

MacCallum, Hypogammaglobulinaemia in the United Kingdom, Medical Research Council special report series, No 310, pps 72-85.

Minor et al 1983, Location and primary structure of a major antigenic site for poliovirus neutralization, Nature 301 674-679.

Racaniello and Baltimore, Cloned poliovirus complementary DNA in infections in mammalian cells, Science 214 916-919.

Schild et al, 1980, J. Gen. Virl. 51 157-170

Stanway et al, 1983, The nucleic acid sequence poliovirus type 3 Leon 12a$_1$b; comparison with type 1, Nucleic Acids Research 11 5629-5643.

Stanway et al, 1984, Comparison of the complete nucleotide sequences of the genomes of the neurovirulent polovirus P3/Leon/37 and its attenuated Sabin vaccine derivative P3/Leon/12a$_1$b, Proc. Natl. Acad. Sci. U.S.A. 81 539-1543.

TABLE 1

| poliovirus codon | 286 | 287 | 288 | 289 | 290 |
|---|---|---|---|---|---|
| type 3 | | | | | |
| Sabin | Arg | Asn | Asn | Leu | Asp |
| Leon | Lys | Asn | Asn | Leu | Asp |
| mutant a (Example 1) | Arg | Asp | Asn | Leu | Asp |
| mutant b (Example 1) | Arg | Asn | Asp | Leu | Asp |
| mutant c (Example 2) | Arg | Asn | Asn | Leu | Glu |
| poliovirus codon | 286 | 287 | 288 | 289 | 290 |
| type 2 | | | | | |
| Sabin | Lys | Asp | Gly | | Leu | Thr |

| poliovirus codon | 287 | 288 | 289 | 290 | 291 | 292 |
|---|---|---|---|---|---|---|
| type 1 | | | | | | |
| Sabin | Lys | Asp | Gly | Thr | Leu | Thr |
| Mahoney | Lys | Asp | Gly | Thr | Leu | Thr |

TABLE 2

Reactions of representatives of 342 antigenic mutant viruses with monoclonal antibodies

| Virus strain | 25-1-14 | 25-4-12 | 27-4-4 | 199 | 194 | 134 | 208 | 175 | 204 | 197 | 165 | 198 |
|---|---|---|---|---|---|---|---|---|---|---|---|---|
| P3 Leon USA/1937 | | | | | | | | | | | | |
| 1 | r | r | | r | | | | | | r | | r |
| 2 | r | r | | r | r | | | | | r | r | r |
| 3 | r | r | r | r | r | | r | r | r | r | r | r |
| 4 | r | r | r | r | r | | r | | r | r | r | r |
| 5 | | | | r | r | r | r | r | | r | r | r |
| 6 | | | | r | r | r | r | | | | r | |
| 7 | | | | r | r | r | r | r | r | | r | |
| 8 | | r | | | r | r | | | | r | | r |
| 9 | r | r | r | r | r | r | r | | r | r | r | r |

TABLE 2-continued

Reactions of representatives of 342 antigenic mutant viruses with monoclonal antibodies

| Virus strain | 25-1-14 | 25-4-12 | 27-4-4 | 199 | 194 | 134 | 208 | 175 | 204 | 197 | 165 | 198 |
|---|---|---|---|---|---|---|---|---|---|---|---|---|
| 10 | r | | r | r | r | r | r | r | r | r | r | r |
| 11 | | | | r | r | | r | r | | r | r | |
| 12 | | r | | r | r | r | r | r | | | r | r |
| 13 | r | r | | r | | r | r | r | | | r | r |
| 14 | r | r | | | | | | r | | r | r | |
| 15 | r | r | r | r | r | | | r | r | r | r | r |
| 16 | r | r | | r | r | | r | | r | | r | r |
| Sabin | | | | | | | | | | | | |
| Leon | | | | | | | | | | | | |
| 12a₁b | | | | | | | | | | | | |
| A | r | r | r | r | r | | r | r | r | r | r | r |
| B | r | r | r | r | r | | | r | r | r | r | r |
| D | r | r | r | r | r | r | r | r | r | r | r | r |
| E | r | r | r | r | r | r | r | r | | r | | r |
| F | r | r | r | r | r | | r | | r | r | r | |
| G | | r | | r | r | r | r | r | | | r | r |
| I | | r | | | | | | | | | | r |
| J | | | | r | r | r | r | | | | r | |
| K | | | | r | r | r | r | r | r | | r | |
| L | | | | r | r | r | r | r | | r | r | |
| M | | | | r | | | r | | | r | r | |
| N | | | | r | | r | r | | | | r | |
| O | | | | r | r | | r | r | | r | r | |
| P | | r | | r | r | r | r | r | r | | r | r |
| Q | | | | | | r | r | | | | | |

Mutant viruses were said to be sensitive to antibody if a 1:10 dilution of antibody as ascitic fluid was able to preserve a cell sheet from challenge with $10^4$ $TCID_{50}$ virus during incubation at 35° for 2 days. Results were checked by plaque assay in the presence of dilutions of antibody.
r indicates resistance

TABLE 3

Reaction of mutants of type 3 poliovirus with monoclonal antibodies by neutralisation

| | 204 | 138 | 1023[a] | 840[a] | 251[a] | 557[a] | 1084[a] | 1007[a] | 961[a] | 792[b] | 248[a] | 665[a] | 756[a] |
|---|---|---|---|---|---|---|---|---|---|---|---|---|---|
| 1 | / | | | | | | | | | | | | |
| 2 | | / | / | | / | | | / | | | | | |
| 3 | | | / | / | / | / | / | | | | | | |
| 4 | | | / | / | / | / | / | | | | | | |
| 5 | | | / | / | / | | | / | | | | | |
| 6 | | / | / | / | / | / | / | / | | | | | |
| 7 | | | | | | | | | / | | | | |
| 8 | | | | | | | | | / | | | | |
| 9 | | | | | | | | | | / | / | / | |
| 10 | | | | | | | | | | / | / | / | |
| 11 | | | | | | | | | | / | | / | / |
| 12 | | | | | | | | | | / | | / | / |
| 13 | | | | | | | | | | | | / | / |

[a]antibody generated from mice immunised with trypsin treated sabin type 3 virus
[b]antibody generated from mice immunised with native P3/Finland/23127/1984

TABLE 4

Location of amino acid substitutions in antigenic mutants of type 3 poliovirus

| Mutant | Protein | Amino acid |
|---|---|---|
| 1 | VP1 | $Arg_{98}$-Gly |
| 2 | VP1 | $Asn_{287}$-Asp |
| 3 | VP3 | $Glu_{58}$-Asn |
| 4 | VP3 | $Ser_{59}$-Asn |
| 5 | VP3 | $Ser_{59}$-Arg |
| 6 | VP1 | $Asp_{290}$-Glu |
| 7 | VP3 | $Asp_{77}$-Glu |
| 8 | VP3 | $Ser_{79}$-Leu |
| 9 | VP2 | $Thr_{167}$-Lys |
| 10 | VP2 | $Val_{166}$-Ala |
| 11 | VP2 | $Glu_{172}$-Ala |
| 12 | VP2 | $Glu_{172}$-Lys |
| 13 | VP2 | $Asn_{164}$-Lys |
| | VP2 | $Asn_{164}$-Thr |

TABLE 5

Antibody titres of rabbits immunised with BTG coupled peptide 2 with homologous peptide

| Rabbit | Day 0 | Day 20 | Day 41 |
|---|---|---|---|
| 237 | <100 | <100 | 800 |
| 238 | <100 | <100 | 1600 |
| 239 | <100 | <100 | 200 |
| 240 | <100 | 100 | 6400 |

TABLE 6

Antibody titres to peptide 1 in rabbits immunised with BTG coupled peptide 1

| Rabbit | Day 0 | Day 17 | Day 37 |
|---|---|---|---|
| 256 | <100 | 400 | 6400 |
| 257 | <100 | 1600 | 12800 |
| 258 | <100 | 1600 | >12800 |
| 259 | <100 | 1600 | 12800 |

TABLE 7

Antigen blocking antibodies to Sabin type 3 C antigen in rabbits immunised with peptide 2

|     | Day 0 | Day 17 | Day 31 | Day 53 |
|-----|-------|--------|--------|--------|
| 237 | <5    | <5     | 5      | 40     |
| 238 | <5    | <5     | 20     | 40     |
| 239 | <5    | <5     | 10     | 5      |
| 240 | <5    | <5     | <5     | 10     |

TABLE 8

Antigen blocking titres to C antigen of various stains of poliovirus type 3 in rabbits immunised with peptide 2 on day 53 (after 3 doses peptide

| Strain | Difference in sequence from SP6 | Rabbit 237 | 238 | 239 | 240 |
|--------|-------------------------------|-----|-----|-----|-----|
| SP6    | —                             | 20  | 40  | 5   | 10  |
| Leon   | VP1 287                       | 20  | 40  | 10  | 5   |
| 306    | VP1 88–100                    | 20  | 20  | 10  | 5   |
| 183    | VP1 88–100                    | 20  | 40  | 10  | 5   |
| 63.1.9 | 3 changes VP1 88–100          | 10  | 20  | 10  | 10  |

TABLE 9

Antigen blocking titres against type 3 C antigen in animals immunised with peptide 1

| Rabbit | Day 0 | Day 17 | Day 37 | Day 64 |
|--------|-------|--------|--------|--------|
| 256    | <5    | <5     | 80     | 20     |
| 257    | <5    | 20     | >320   | 1280   |
| 258    | <5    | 5      | >320   | ND     |
| 259    | <5    | <5     | 10     | <5     |

We claim:

1. A synthetic peptide, suitable for use in vaccination against or diagnosis of a disease caused by an enterovirus, which is a peptide coded for by codons 286 to 288 in the RNA sequence coding for the structural capsid protein VP1 of poliovirus type 3 Sabin strain or by equivalent codons of another enterovirus or is an antogenic equivalent of such a peptide, the antigenic equivalent being:
   (i) a said peptide modified by the inclusion therein of one or more changes to the amino acid sequence;
   (ii) a first longer peptide which incorporates the sequence of a said peptide or a said modified peptide and which has up to four extra amino acid residues attached to the C-terminal end of the said sequence or up to four extra amino acid residues attached to the N-terminal end of said sequence or up to four extra amino acid residues attached to the C-terminal end and up to four extra amino acid residues attached to the N-terminal end of said sequence;
   (iii) a second longer peptide which incorporates the sequence of a said peptide, a said modified peptide or a said first longer peptide, to which sequence is linked directly, by means of a further amino acid residue or by means of a disulphide bridge between Cys residues attached to each sequence of up to eighteen amino acid residues which comprises a hexapeptide sequence coded for by codons 93 to 98 in said RNA sequence or by equivalent codons of another enterovirus; or
   (iv) a third longer peptide which incorporates the sequence of a said peptide, a said modified peptide or a said first longer peptide, to which sequence is linked directly, by means of a further amino acid residue or by means of a disulphide bridge between Cys residues attached to each sequence, a sequence comprising residues 58 and 59 of the VP3 capsid protein of an enterovirus of the same type but starting with a residue numbered no lower than 53 and ending with a residue numbered no higher than 68;
   each said antigenic equivalent being capable of raising antobodies capable of neutralizing the same strain and type of enterovirus as said peptide to which said antigenic equivalent corresponds and the numbers of the codons being counted from the 5'-terminus of the nucleotide sequence for the VP1 capsid protein.

2. The peptide of claim 1, suitable for use in vaccination against or diagnosis of a disease caused by type 3 poliovirus, which comprises the sequence:

$$A_0\text{-}A_1\text{-}A_2 \qquad (I)$$

in which $A_0$ is Arg or Lys and each $A_1$ and $A_2$ is independently Asn or Gln or $A_0$ is Arg and each of $A_1$ and $A_2$ is independently Asp or Glu.

3. The peptide of claim 2, wherein $A_0$ is Arg, $A_1$ is Asn and $A_2$ is Asn.

4. The peptide of claim 3, which comprises the sequence:

Gly-Val-Asp-Tyr-Arg-Asn-Asn-Leu-Asp-Pro-Leu.

5. The peptide of claim 1, suitable for use in vaccination or diagnosis of a disease caused by type 2 poliovirus, which comprises the sequence:

Lys-A'$_1$-Gly in which A'$_1$ is Asp or Glu.

6. The peptide of claim 5, which comprises the sequence:

Gly-Val-Asp-Tyr-Lys-Asp-Gly-Leu-Thr-Pro-Leu.

7. The peptide of claim 1, suitable for use in vaccination against or diagnosis of a disease caused by type 1 poliovirus, which comprises the sequence:

$$\text{Lys-}A_4\text{-Gly-}A_5 \qquad (III)$$

in which $A_4$ is Asp or Glu and $A_5$ is Ser or Thr.

8. The peptide of claim 7, in which $A_4$ is Asp and $A_5$ is Thr.

9. The peptide of claim 8, which comprises the sequence:

Gly-Val-Asp-Tyr-Lys-Asp-Gly-Thr-Leu-Thr-Pro-Leu.

10. The peptide of claim 1, which further has a Cys residue at one or both ends.

11. A synthetic peptide, suitable for use in vaccination or diagnosis of a disease caused by an enterovirus, which is a peptide coded for by codons 286 to 290 in the RNA sequence coding for the structural capsid protein VPI of poliovirus type 3 Sabin strain or by equivalent codons of another enterovirus or is an antigenic equivalent of such a peptide, the antigenic equivalent being:
   (i) a said peptide modified by the inclusion therein of one or more changes to the amino acid sequence,
   (ii) a first longer peptide which incorporates the sequence of a said peptide or a said modified peptide and which has up to four extra amino acid residues attached to the C-terminal end of said sequence or up to four extra acid residues attached to the N-terminal end of said sequence or up to four amino acid residues attached to the C-terminal end and up to four extra amino acid residues attached to the N-terminal end of said sequence;

(iii) a second longer peptide which incorporates the sequence of a said peptide, a said modified peptide or a said first longer peptide, to which sequence is linked directly, by means of a further amino acid residue or by means of a disulphide bridge between Cys residues attached to each sequence, a sequence of up to eighteen amino acid residues which comprises a hexapeptide sequence coded for by codons 93 to 98 in said RNA sequence or by equivalent codons of another enterovirus; or (iv) a third longer peptide which incorporates the sequence of a said peptide, a said modified peptide or a said first longer peptide, to which sequence is linked directly, by means of a further amino acid residue or by means of a disulphide bridge between Cys residues attached to each sequence, a sequence comprising residues 58 and 59 of the VP3 capsid protein of an enterovirus of the same type but starting with a residue numbered no lower than 53 and ending with a residue numbered no higher than 68;

each said antigenic equivalent being capable of raising antobodies capable of neutralizing the same strain and type of enterovirus as said peptide to which said antogenic equivalent corresponds and the numbers of the codons being counted from the 5'-terminus of the nucleotide sequence coding for the VP1 capsid protein.

12. The peptide of claim 11, suitable for use in vaccination against or diagnosis of a disease caused by type 3 poliovirus, which comprises the sequence:

$$A_0\text{-}A_1\text{-}A_2\text{-Leu-}A_3 \qquad (I)$$

in which (i) $A_0$ is Arg, each of $A_1$ and $A_2$ is independently Asn or Gln and $A_3$ is Asp or Glu or (ii), with the others of $A_0$ to $A_3$ being defined under (i), $A_0$ is Arg or $A_1$ or $A_2$ is Asp or Glu.

13. The peptide of claim 12, wherein $A_0$ is Arg, $A_1$ is Asn, $A_2$ is Asn and $A_3$ is Asp.

14. The peptide of claim 13, which comprises the sequence:

Gly-Val-Asp-Tyr-Arg-Asn-Asn-Leu-Asp-Pro-Leu.

15. The peptide of claim 11, suitable for use in vaccination or diagnosis of a disease caused by type 2 poliovirus, which comprises the sequence:

Lys-$A'_1$-Gly-Leu-$A'_3$ in which $A'_1$ is Asp or Glu and $A'_3$ is Thr or Ser.

16. The peptide of claim 15, which comprises the sequence:

Gly-Val-Asp-Tyr-Lys-Asp-Gly-Leu-Thr-Pro-Leu.

17. The peptide of claim 11, suitable for use in vaccination against or diagnosis of a disease caused by type 1 poliovirus, which comprises the sequence:

$$\text{Lys-}A_4\text{-Gly-}A_5\text{-Leu-}A_6 \qquad (III)$$

in which $A_4$ is Asp or Glu and each of $A_5$ and $A_6$ is independently Ser or Thr.

18. The peptide of claim 17, in which $A_4$ is Asp and $A_5$ and $A_6$ are both Thr.

19. The peptide of claim 18, which comprises the sequence:

Gly-Val-Asp-Tyr-Lys-Asp-Gly-Thr-Leu-Thr-Pro-Leu.

20. The peptide of claim 11, which further has a Cys residue at one or both ends.

21. A synthetic peptide, suitable for use in vaccination against or diagnosis of a disease caused by a poliovirus, which is a peptide coded for by codons 286 to 288 in the RNA sequence coding for the structural capsid protein VP1 of poliovirus type 3 Sabin strain or by equivalent codons of another poliovirus or is an antigenic equivalent of such a peptide, the antigenic equivalent being:

(i) a said peptide modified by the inclusion therein of one or more changes to the amino acid sequence;

(ii) a first longer peptide which incorporates the sequence of a said peptide or a said modified peptide and which has up to four extra amino acid residues attached to the C-terminal end of the said sequence or up to four extra amino acid residues attached to the N-terminal end of said sequence or up to four extra amino acid residues attached to the C-terminal end and up to four extra amino acid residues attached to the N-terminal end of said sequence; or (iii) a second longer peptide which incorporates the sequence of a said peptide, a said modified peptide or a said first longer peptide, to which sequence is linked directly, by means of a further amino acid residue or by means of a disulphide bridge between Cys residues attached to each sequence, a sequence of up to eighteen amino acid residues which comprises a hexapeptide sequence coded for by codons 93 to 98 in said RNA sequence or by equivalent codons of another poliovirus;

each said antigenic equivalent being capable of raising antibodies capable of neutralizing the same strain and type of poliovirus as said peptide to which said antigenic equivalent corresponds and the numbers of the codons being counted being the 5'-terminus of the nucleotide sequence coding for the VP1 capsid protein.

* * * * *